US006966911B2

(12) United States Patent
Groiso (10) Patent No.: US 6,966,911 B2
(45) Date of Patent: Nov. 22, 2005

(54) BONE STAPLE AND METHODS FOR CORRECTING BONE DEFICIENCIES BY CONTROLLABLY SUPPRESSING AND/OR INDUCING THE GROWTH OF THE EPIPHYSEAL PLATE

(76) Inventor: Jorge Abel Groiso, Arenales 2245, 1°-Capital Federal - Buenos Aires (AR)

( * ) Notice: Subject to any disclaimer, the term of this patent is extended or adjusted under 35 U.S.C. 154(b) by 275 days.

(21) Appl. No.: 10/051,156

(22) Filed: Jan. 22, 2002

(65) Prior Publication Data

US 2003/0139746 A1    Jul. 24, 2003

(51) Int. Cl.$^7$ ............................................. A61B 17/58
(52) U.S. Cl. ....................................................... 606/75
(58) Field of Search ............................ 606/60, 72, 75, 606/73, 78, 86, 105; 411/457, 458, 475

(56) References Cited

U.S. PATENT DOCUMENTS

| 5,246,443 A | * | 9/1993 | Mai ............................ 606/78 |
| 5,425,407 A | * | 6/1995 | Archuleta et al. .......... 152/370 |
| 5,785,713 A | * | 7/1998 | Jobe ............................ 606/69 |
| 6,059,787 A | * | 5/2000 | Allen .......................... 606/75 |
| 6,554,852 B1 | * | 4/2003 | Oberlander .................. 606/232 |
| 6,783,531 B2 | * | 8/2004 | Allen .......................... 606/75 |

FOREIGN PATENT DOCUMENTS

FR            2694696          * 2/1994

* cited by examiner

Primary Examiner—Eduardo C. Robert
(74) Attorney, Agent, or Firm—Michael Bednarek; Pillsbury Winthrop Shaw Pittman LLP (57) ABSTRACT

A bone staple for repairing bones and/or correcting bone deficiencies by controlling the growth of the epiphyseal plate, the staple comprising a body comprising a cross bar and at least two legs extending from the cross bar, the legs being designed for introducing into the bone. The body is made of a shape memory alloy and the legs normally diverge from each other defining spring legs tending to move apart from each other under a compression force, whereby a lengthening of the epiphyseal plate is induced. Preferably, the cross bar extends beyond the connection to the legs and forms stop means for abutting the bone and keep the cross bar spaced apart from the epiphyseal plate. Additionally, each leg includes an helical thread designed for anchoring into the bone, for firmly retaining the staple into the bone and for unscrewing the legs once the stable should be removed.

4 Claims, 5 Drawing Sheets

BONE STAPLE AND METHODS FOR CORRECTING BONE DEFICIENCIES BY CONTROLLABLY SUPPRESSING AND/OR INDUCING THE GROWTH OF THE EPIPHYSEAL PLATE

BACKGROUND OF THE INVENTION

1. Field of the Invention

The present invention relates to the medical field and particularly to orthopaedics and traumatology for the correction of limb bone deformities and deficiencies. More particularly, the invention relates to a surgical implant or staple and method for repairing bones and/or correcting limb inequality and most preferably the invention relates to methods and staples for correcting bone deficiencies by suppressing and/or inducing the growth of the epiphyseal plate in the bone. Additionally, the invention relates to staples with enhanced osseous integrating means capable of being easily removed from the bone even once integrated. Furthermore, the invention relates to staples for preventing the perichondrium and the periosteal vascular ring from damage when installing the staple into the bone.

While more specific reference to the control of growth plate or epiphyseal plate will be made in the present disclosure and drawings, the bone implant and methods of the invention are not restricted to this specific application but they may be applied to any other field where a prosthesis, a fixation device, etc. is to be secured into a bone or a broken bone is to be repaired by joining its broken pieces. In addition, the term "patient" is applicable either to animals or human beings.

2. Description of the Prior Art

Length discrepancies and angular deformities of the limbs are quite frequent among children and provoked by several causes such as congenital, post-trauma, post-infection, oncologic causes, etc. The need exists for correcting these abnormalities because of function and aesthetic reasons. The treatment of some of these childhood deformities is based on the concept of mechanically suppressing growth.

Bone staples are well known in the orthopaedics and traumatology, such as in techniques for correcting angular deviations of limbs, genu valgum for example, by unilateral restriction of the growth plate.

For correcting angular deviations the mechanical suppression can be obtained by temporary using metal staples across the growth plate, at unilateral locations, at the convex side of the deformity, for example. The staples are removed once the correction has been reached.

For correcting length abnormalities, the lengthening of the bone is obtained by using an external fixator and the shortening of the limb is obtained by arresting or suppressing the growth plate at even locations around the bone.

The technique of mechanical suppression by temporary using an external fixator is carried out by installing the fixator in the limb, on the concave bone side, for producing a slow stretching of the growth plate. This mechanical technique is known as epiphyseal distraction.

More precisely, epiphyseal distraction is a surgical technique that is widely used to lengthen an abnormal bone or correct physeal deviations prior to growth plate closure. This technique, also called "chondrodiatasis", involves slow, gradual, symmetric distraction of the growth plate. The term "hemichondrodiatasis", on the other hand, is used to refer to the technique of asymmetric distraction of the growth plate for correction of epiphyseal-diaphyseal deviations.

Since the use of external fixators for the above described mechanical suppressing techniques has shown to be expensive as well as traumatic and cumbersome for the patient, and the fixator leaves unsightly scars, the use of this device has not widely and intensively imposed. It would be desirable to use staples for these techniques, however, the staples are affected by several disadvantages and drawbacks that caused them to be not widely imposed in the medical field.

As it was stated above, angular deviations or deformities and length discrepancies of the limbs, for example, are often treated with staples. After staples are placed across a growth plate, further growth of this plate increases the pressure on the inner surfaces of the staple legs. This increased pressure, which has been measured about 1 Mpa, slows bone growth within and near the staple, i.e. in the region between the legs, and, simultaneously, forces the staple legs apart. This pressure from the cartilage plate, together with the legs moving away from each other, causes the legs to be extruded and expelled out from the bone thus loosing the grip in the bone.

Another drawback the physicians have found with the use of staples is that the same do not work satisfactorily because the bone growth is not restarted afterwards, thus producing the appearance of opposite deformity due to the constant growth of the cartilage of the side that was not operated upon. An explanation for this effect is that, presumably, a damage is inflicted on the perichondrium or the perichondrial vessels when the staples are inserted into physis. Generally, the staples are provided with reinforcing squares at the inner side thereof, that is at the inner corners formed by the connection between the cross bar and legs. As the staple is hammered up to abutting the external surface of the bone, the reinforcements, as well as the flat bridge or cross bar enter into contact with the growth plate and damage the perochondrium and the perichondrial vessels, this being the cause of the undesired epiphysial arrest.

As indicated above in connection with one of the drawbacks of using staples, the pressure exerted by the growing cartilage plate causes the staple legs to open, extrude and slide out of the bone. Many staples of the prior art has attempted to prevent the staple from sliding out the bone by providing the staple legs with barbs or protrusions to enhance the anchoring of the legs into the bone mass. However, when deformation has been corrected and the temporary staple must be removed from the bone, the anchorage of the legs into the growing bone mass, that is desired at the time the stable is to be retained into the bone, is a bar or obstacle at the time the staple must be removed. In effect, this firm osseous anchorage prevents the staple from being easily removed by normal forces and operations.

It would be therefore desirable and convenient to have a bone staple:

capable of accommodating to the growing force of the cartilage plate, capable of being firmly retained and anchored into the bone to prevent the sliding out effect but capable of being easily removed when necessary, particularly after osseous anchorage, and capable of being hammered into the bone without the bridge or cross bar of the staple damaging the perochondrium, the perichondrial vessels, and/or any other part of the bone.

SUMMARY OF THE INVENTION

It is therefore an object of the present invention to provide an expansion bone staple for correcting bone deficiencies by controlling the growth of the epiphyseal plate, the staple comprising:

a shape memory material body comprising a cross bar and at least two legs extending from the cross bar and normally diverging from each other, wherein the legs define spring legs tending to expand apart from each other when subject to a compression force, whereby when the staple is introduced into a bone with each leg at each side of the epiphyseal plate under a compression force bringing the legs to be closer than in a normal position the legs exert a expansion force for lengthening the epiphyseal plate while the cross bar keeps a normal length thereof forming a tether for a periphery of the epiphyseal plate, thus causing the epiphyseal plate to growth around a focus.

It is still another object of the present invention to provide a method for installing said expansion staple into a bone, for correcting bone deficiencies by controlling the growth of the epiphyseal plate, the method comprising:

i. providing said staple with the legs normally diverging from each other, ii. applying a compression force to the legs and bringing the legs into a substantially parallel position, and ii. nailing the staple into the bone with at least one leg nailed at each side of the epiphyseal plate, whereby the staple will be retained into the bone with the legs exerting an expansion force over the epiphyseal plate while the cross bar will exert a suppression effect on the periphery of the epiphyseal plate.

It is a further object of the present invention to provide an abutting bone staple for correcting bone deficiencies by controlling the growth of the epiphyseal plate, the staple comprising:

a body comprising a cross bar and at least two legs extending from the cross bar, wherein the cross bar extends beyond a corner joint with the legs and forms stop means for abutting the bone, the cross bar defining an arc shape extending between the legs and at a level higher than the stop means, whereby when the staple is installed into the bone the arc shaped cross bar remains spaced apart from the epiphyseal plate.

It is even another object of the present invention to provide a method for installing the above mentioned abutting bone staple, for correcting bone deficiencies by controlling the growth of the epiphyseal plate, the method comprising:

i. providing said staple, ii. placing the staple with the cross bar spanning across the epiphyseal plate, and iii. nailing the staple into the bone with at least one leg nailed at each side of the epiphyseal plate, whereby the stop means abut against the bone at each side of the epiphyseal plate and the arc shaped cross bar remains spaced apart from the epiphyseal plate.

It is even another object of the present invention to provide a screw bone staple for repairing bones and correcting bone deficiencies, the staple comprising:

a body comprising a cross bar and at least two legs extending from the cross bar, wherein each leg includes an helical thread designed for anchoring into the bone, the cross bar being designed to be cut whereby once the bone deficiency is overcome and the staple is anchored the cross bar is cut and each leg is unscrewed and removed from the bone.

It is even another object of the present invention to provide a method for installing and removing the above mentioned screw bone staple, for repairing bones and correcting bone deficiencies, the method comprising:

i. providing said staple, ii. installing the staple by inserting the legs of the staple into the bone, iii. waiting for a period of time enough for repairing the bone or correcting the bone deficiency, wherein the staple legs are anchored into the bone, iv. cutting the cross bar in a location between the legs, and v. removing each leg from the bone by gripping and unscrewing the leg from the bone.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 1:
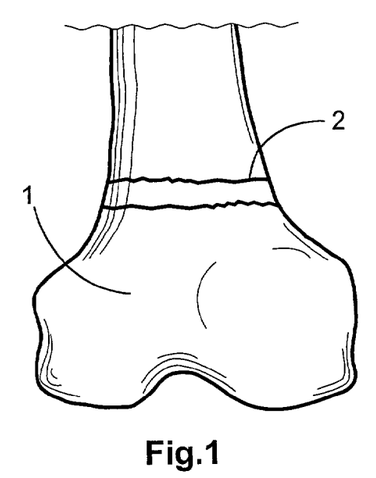
FIG. 1 shows a diagrammatic side elevation view of a femur head with a normal physis.
Figure 2:
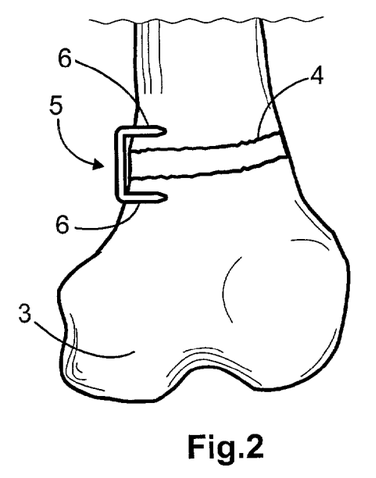
FIG. 2 shows a diagrammatic side elevation view of a femur head with an abnormal angled physis and a staple of the prior art installed into the bone for controlling the growth of the epiphyseal plate.
Figure 3:
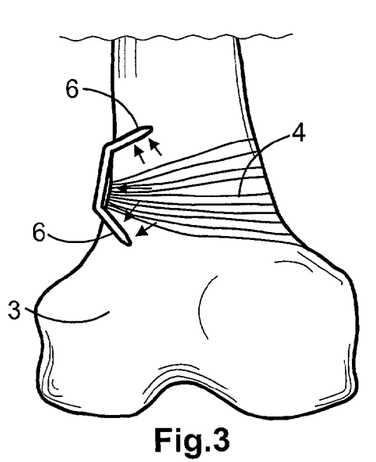
FIG. 3 shows a diagrammatic side elevation view of the femur head of FIG. 2 after a period of time has passed from the surgery, with the staple being expanded against the compression force of the staple legs.
Figure 4:
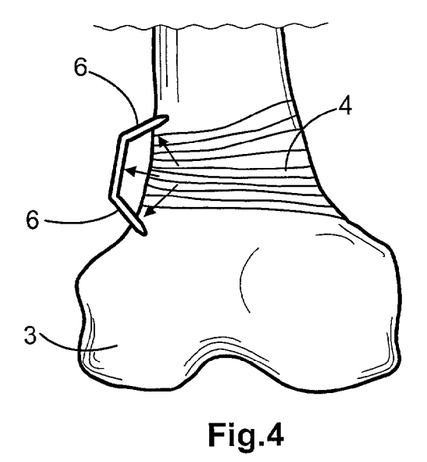
FIG. 4 shows a diagrammatic side elevation view of the femur head of FIG. 3 after a further period of time, with the staple slipped out the bone under the expansion force of the cartilage plate.

Now referring in detail to the drawings it may be seen from FIG. 1 a normal bone, particularly a femur head 1 having a normal epiphyseal or growth plate 2 whereby the femur growths normally along a normal longitudinal axis of the bone. When the bone, such as bone 3, includes an abnormal growth plate, an angled plate 4 as shown in FIGS. 2–4, for example, the bone tends to growth along a line deviated out from the normal bone axis, thus providing the bone with a convex side and a concave side. Depending of the location of this abnormalities the patient will be affected of a genu valgum or varum. FIG. 2 clearly shows that the left bottom portion or protrusion of bone 3 is larger than the right one, therefore a bottom bone (not illustrated) that is joined to bone 3, will be deviated from a common axis (see FIG. 6).

In order to suppress the growth at the left side and induce or allow the growth at the right side, a prior art staple 5 is nailed or installed in other way into the bone, with the staple legs 6 inserted at each side of plate 4 (FIGS. 2–4). During growth, plate 4 exerts an expansion force, indicated by arrows in FIGS. 3, 4, forcing legs 6 to move away from each other. This forces also extrude the legs into the bone mass. After a period of time from surgery, 5–7 months for instance, legs 6 are finally expelled from the bone and appears slipped out the bone as shown in FIG. 4, thus loosing the grip into the bone and failing in controllably suppressing the plate growth. FIGS. 3, 4 show the bottom right side of bone end 3 having a size larger than the one illustrated in FIG. 2 because this right side has grown more than the left side thank to the suppression exerted by the staple. The growing would be completed, however, if the staple would not be expelled from the bone.

Figure 5:
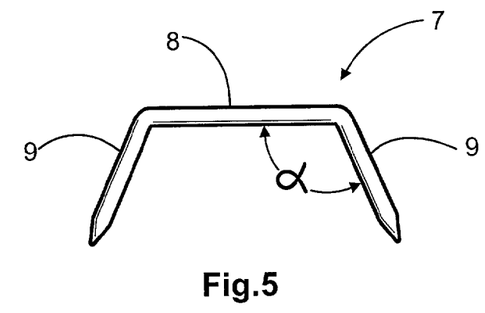
FIG. 5 shows a side elevational view of a bone staple according to a preferred embodiment of the invention.

In order to prevent the slipping out of the staple as well as for controlling the growth plate by inducing growth in the central regions thereof but arresting the periphery of same, the inventor has developed the staple of FIG. 5. The inventive staple, also named as expansion staple, indicated by generic reference number 7, is preferably for correcting bone deficiencies by controlling the growth of the epiphyseal plate, and the staple comprises a shape memory material body, preferably made of a resilient metal or alloy, and most preferably made of nitinol. The staple body includes a bridge or cross bar 8 and at least two legs 9 extending from the cross bar. Legs 9 normally diverge from each other, as shown in FIG. 5, whereby the same define spring legs that tend to keep their open or diverging normal, or resting, position and to exert a resilient expansion force when subject to a compression force, 2. Each leg normally defines an angle α of between about 91° to about 180° degrees relative to the cross bar, preferably an angle between 105° and 185°, and most preferably 135°.

Figure 6:
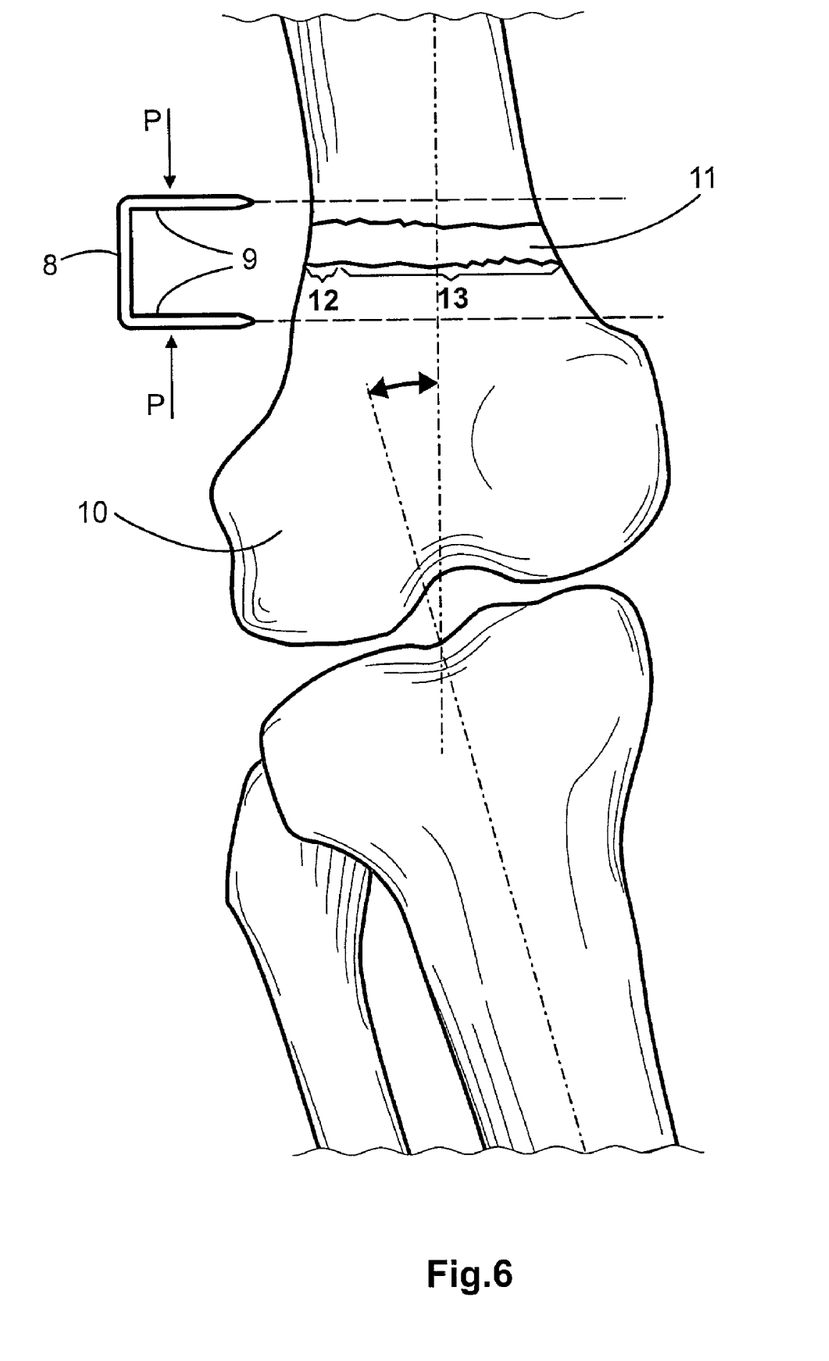
FIG. 6 is a diagrammatic side elevational view of a femur head with an abnormal growth plate and the staple of FIG. 5 with its legs brought into a parallel position under a compression force, ready to be inserted into the bone, across the plate.
Figure 7:
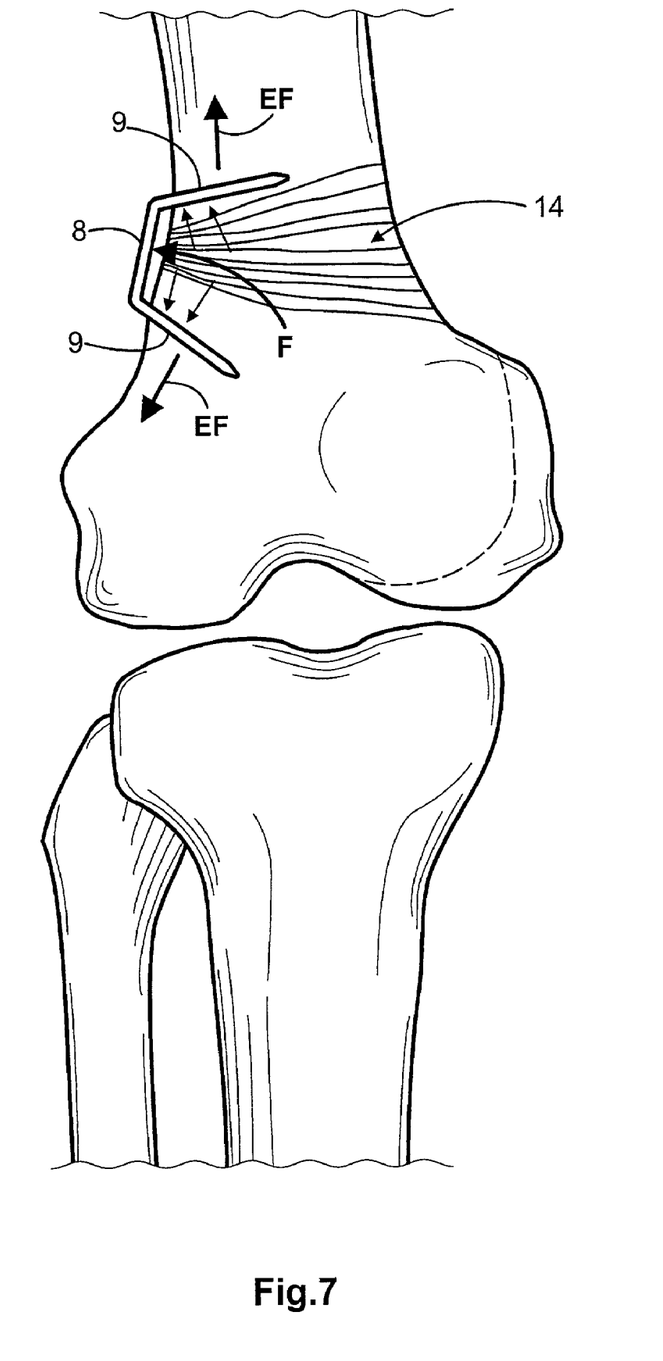
FIG. 7 shows a diagrammatic side elevation view of the femur head of FIG. 6 after a period of time has passed from the surgery, with the staple diverged into a substantial normal position, as shown in a resting position in FIG. 5, but completely inserted into bone and not slipped out as it occurs in the prior art (FIG. 4)

Also according to the invention, a method is provided for installing staple 7 into an upper bone 10 as shown in FIGS. 6, 7. FIG. 6 clearly shows that the upper bone has an abnormal bottom right side which is smaller than the bottom left side, this causing the bottom bone of the limb extending out of a normal axis and forming an angle with the axis of the upper bone 10. If both sides of the bottom end of bone 10 would be normal, having the same size, the bottom bone would join bone 10 along the same common axis. According to the method, staple 7 is provided with the legs normally diverging from each other, a compression force P is applied to the legs until bringing the same to a desired relative position, preferably a substantially parallel position. To bring the legs into a parallel relationship, the staple, if made of nitinol, may be cooled at a temperature of 0°, for example. Once in this position the staple may be nailed into the bone with at least one leg nailed at each side of abnormal epiphyseal plate 11, whereby the staple will be retained into the bone with the legs exerting an expansion force over the epiphyseal plate while the cross bar will exert an arrest or suppression effect on a periphery 12 of the epiphyseal plate.

Therefore, when the staple is introduced into the bone with each leg at each side of the epiphyseal plate under a compression force bringing the legs to be closer than in a normal position the legs exert a expansion force EF for lengthening the epiphyseal plate while cross bar 8 remains unaltered, that is non deformed, keeping its normal length thus forming a tether for periphery 12 of the epiphyseal plate. This causes the epiphyseal plate to growth around a growing focus F defined at a central region of periphery 12. FIG. 7 clearly illustrates the growth of plate 11 around focus F, thus showing that plate 11 is prevented from growing only at the periphery thereof, arrested by cross bar 8 while the remaining portion 13 of plate 11, namely most part of plate 11, not only is allowed to growth but is induced to growth by the expansion force of spring legs 9. This growing is larger at the right side of plate 11 as indicated by reference number 14. The phantom line at the right side of the bottom end of bone 10 indicates the abnormal former profile of the bottom as appearing in FIG. 6. The right side of the bone has now grown and the bones are normally aligned.

As stated above, the staple may be nailed into the bone and this nailing step may be carried out by drilling orifices in the bone, one orifice for receiving one leg of the staple. Alternatively, the step of nailing may comprise nailing the staple directly into the bone by hammering the staple on the bone.

Figure 8:
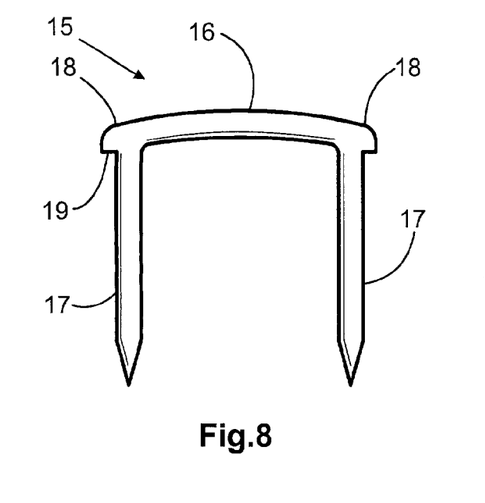
FIG. 8 shows a side elevational view of a bone staple according to another embodiment of the invention.
Figure 9:
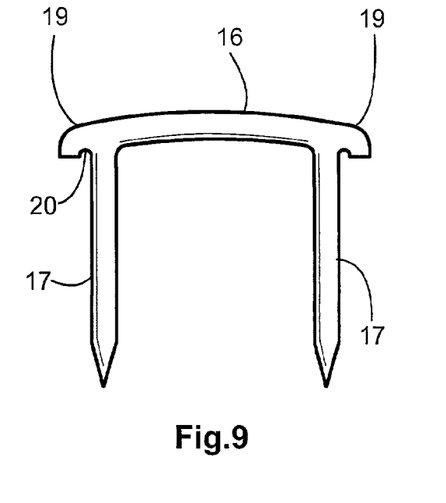
FIG. 9 shows a side elevational view of a bone staple according to a further embodiment of the invention.

According to another embodiment of the invention, the staple shown in FIGS. 8, 9, also named in this application as abutting staple, is designed to prevent the surface bone or the cartilage plate remaining under the cross bar from being damaged from the staple. The staple of FIG. 8, indicated by general reference 15, may be manufactured from a resilient or not material, such as chrome-cobalt alloy, cold-worked 316 SS, medical grade, stainless steel, titanium, nitinol, etc. Staple 15 comprises a bridge or cross bar 16 and legs and is preferably for use in correcting bone deficiencies, either angular or length abnormalities, by controlling the growth of the epiphyseal plate.

Cross bar 16, according to another teaching of the invention, extends beyond a corner joint 18 wherein the bridge is connected to the legs. Thus, stop means 19 are defined in the corner for abutting the bone when the staple is hammered or nailed through other way to the bone level. In addition, the cross bar defines an arc shape (FIG. 8) extending between the legs and at a level higher than the stop means, whereby when the staple is installed into the bone the arc shaped cross bar remains spaced apart from the bone surface and, preferably from the epiphyseal plate. Cross bar 16 is curved like a beam knee with the highest part thereof at a central point of the bridge.

Preferably, the stop means comprises a shoulder as shown in FIG. 8 or, alternatively, may comprise a shoulder 19, shown in FIG. 9, which shoulder is being curved by means of a notch 20 to prevent stresses concentration. In addition, the stop means, and preferably shoulder 19, forms reinforcing means at each connection between the legs and the cross bar, thus making the staple work like a reinforced staple. The reinforcing means operate o oppose any diverging movement of the legs away from each other. The fact that the reinforcement is defined outside the legs, namely not between the legs as in the prior art staples, prevents the bone or the cartilage plate between the legs from being damaged by any reinforcement. When used spanning across a growth plate, stop means 19 located a level lower than the bridge, prevents the bridge from entering into contact with the growth plate.

Also according to the invention, a method is provided for installing bone staple 15 into a bone for correcting bone deficiencies by controlling the growth of the epiphyseal plate. The staple is provided placed in the bone with the cross bar spanning across the epiphyseal plate, and the staple is nailed into the bone with at least one leg nailed at each side of the epiphyseal plate, whereby stop means 19 abut against the bone at each side of the epiphyseal plate and the arc shaped cross bar remains spaced apart from the epiphyseal plate.

The nailing of the staple may comprise drilling orifices in the bone for receiving the legs of the staple. Alternatively, the staple may be directly nailed into the bone by hammering the staple.

Figure 10:
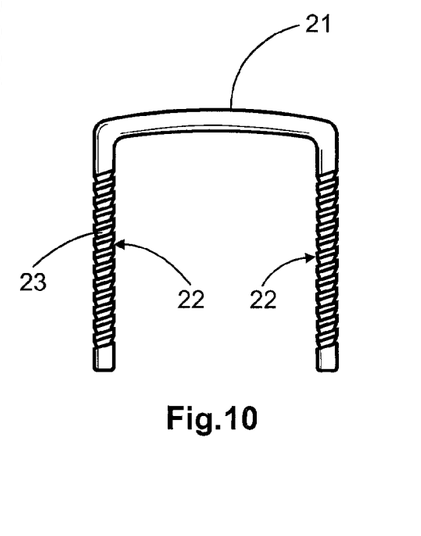
FIG. 10 shows a side elevational view of a bone staple according to a further embodiment of the invention, including unscrewable means for enhancing the anchoring of the staple legs.
Figure 11:
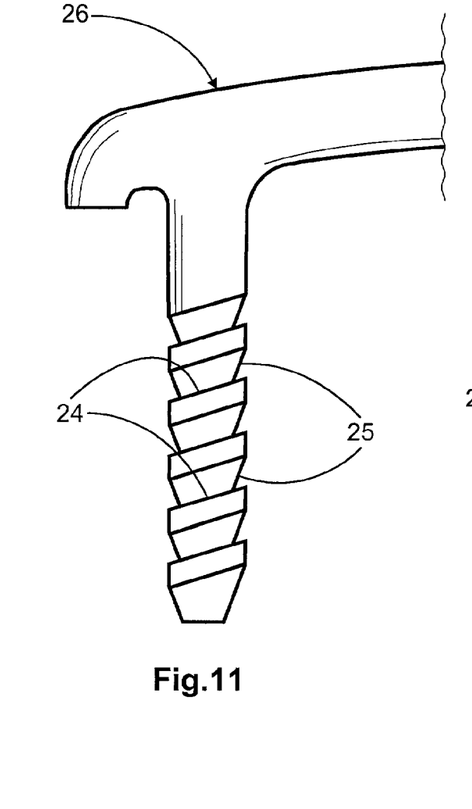
FIG. 11 shows a side elevational partially cross-section view of a further inventive bone staple including unscrewable means for enhancing the anchoring of the legs into the bone.

According to a further embodiment of the invention, the staples shown in FIGS. 10, 11, also named screw staples, are designed to prevent the slipped out thereof from the bone. The inventive bone staple is preferably designed for repairing bones and correcting bone deficiencies, and comprises a body forming a cross bar 21 and at least two legs 22 extending from the cross bar, wherein each leg includes integrating means 23 preferably comprising at least one helical thread designed for anchoring into the bone. In addition, the cross bar is designed for being easily cut by means of any medical tool available at any operation room. The inventive design of osseous anchoring enhancing means 23 permits that, once the bone deficiency is overcome and the staple is osseous anchored the cross bar is cut and each leg is independently unscrewed and removed from the bone.

Osseous anchoring means may be applied to any kind of staple, such as those of FIGS. 5 and 8, 9. As an example, FIG. 11 shows means 23 as applied to the legs of a staple 26, for example a staple according to FIG. 9. While only one leg has been shown it is obvious that means 23 may be applied to all the legs of a staple. As it is better shown in FIG. 11, means 23 comprises a helical thread defining a screw in each leg of the staple. Preferably, thread 23 is defined by a longitudinal cross section comprising an upper flat plane 24 and a lower inclined plane 25, both planes helically extending around the corresponding leg.

Staple 21, including means 23 may be installed according to a method, also provided by the invention, for installing and removing bone staple 21, 26, for repairing bones and correcting bone deficiencies. The method comprises the steps of providing said staple and installing the staple by inserting the legs of the staple into the bone. Once the period of time enough for repairing the bone or correcting the bone deficiency has elapsed, wherein the staple legs are anchored, the cross bar may be cut in a location between the legs, and each leg is independently removed from the bone by gripping the portion cut from the bridge or the leg, and unscrewing the leg from the bone.

The installation of the staple into the bone may be carried out by nailing the staple into the bone, by drilling orifices in the bone for receiving the legs of the staple and nailing the staple into the orifices, or by directly nailing the staple into the bone by hammering the staple on the bone.

Figure 12:
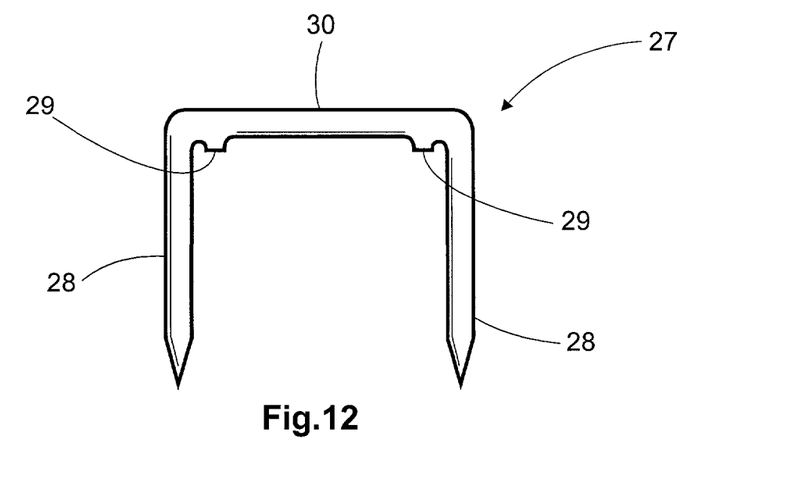
FIG. 12 shows a side elevational view of a bone staple according to a further embodiment of the invention.

According to FIG. 12, another embodiment of the invention is shown, staple 27 comprises stop means 29 located at an inner side of the staple, that is between legs 28. Stop means operate like stop means 19 of the staple shown in FIGS. 8 and 9. In order to prevent the stop means from contacting the growth plate, cross bar 30 will have a length enough to cross above the plate without entering into contact with the cartilage plate. Thus, stop means 29 will contact the bone at each side of the cartilage plate. In addition, stop means 29 will also operate to oppose to any diverging movement of legs 28 away from each other, against the expansion force of the cartilage plate. Therefore, staple 27, like staple 15, will operate like rigid staples.

Figure 13:
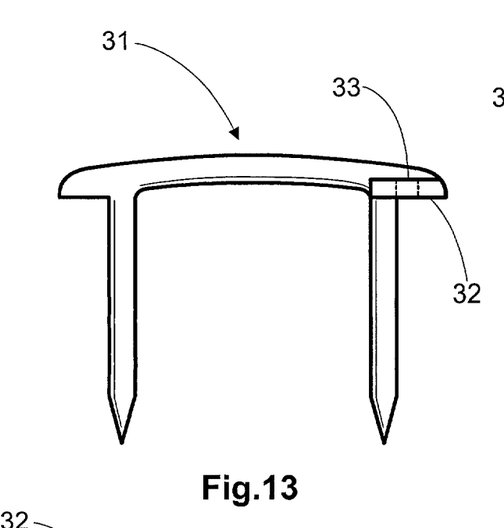
FIG. 13 shows a side elevational view of a bone staple according to another embodiment of the invention.
Figure 14:
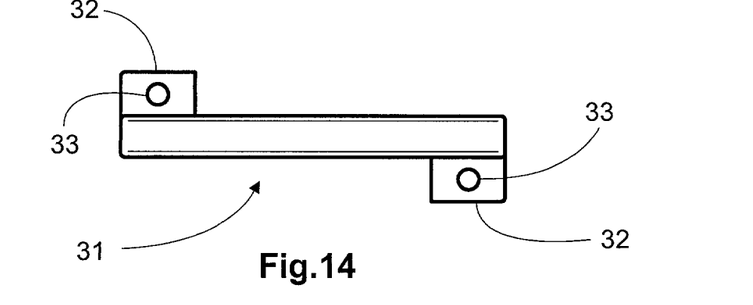
FIG. 14 shows a top plan view of the bone staple of FIG. 13.
Figure 15:
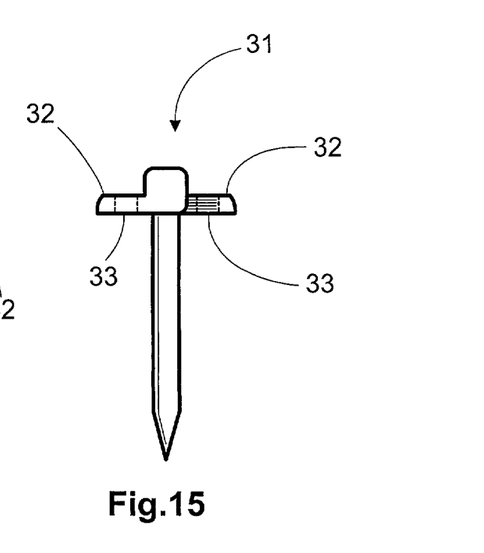
FIG. 15 shows an end elevational view of the bone staple of FIGS. 13 and 14.

Even according to another embodiment of the invention, FIGS. 13–15 show an staple 31 which may be used as a rigid staple or a resilient staple, expansion staple like the one of FIG. 5, depending of the material employed for manufacturing the staple. Furthermore, staple 31 may be provided with stop means like means 19 and 29, and screw means like thread 22 of FIGS. 10, 11. According to the invention, staple 31 is provided with retaining means 32 comprising ears at each side of the cross bar, each ear being designed to receive a fastening means, like a screw, not illustrated, passing through orifices 33. This alternative staple, may be advantageously employed in correcting spine disorders, by fixing the staple into vertebrae.

Depending on the use thereof, the staple of FIG. 12–15 may be installed into a bone by the methods already disclosed in connection to staples of FIGS. 5–11. Also, according to the application, staples of FIGS. 8–15 may be for angular correction or for length correction, thus applied at unilateral location or at uniform spaced apart locations respectively, and may be made of memory shape material, for expansion purposes, or made of rigid materials for compression or suppressing purposes.

While it may not be specifically illustrated, it is remarked that the features of each of the staples illustrated and disclosed herein are capable of being combined selectively or entirely for specific applications. For example, anchoring means 22 may be provided in any of staples 5, 15, 27 and 31, and the diverging-legs design of FIG. 5 may be applied to any of the remaining staples as long as the staple is made of a resilient material or shape memory material or alloy.

While preferred embodiments of the present invention have been illustrated and described, it will be obvious to those skilled in the art that various changes and modifications may be made therein without departing from the scope of the invention as defined in the appended claims.

I claim:

1. A method for installing a staple into a bone, for correcting bone deficiencies by controlling the growth of the epiphyseal plate, the method comprising:
   i. providing a staple comprising a shape memory material body comprising a cross bar and at least two legs extending from the cross bar and normally diverging from each other, wherein the legs define spring legs tending to expand apart from each other when subject to a compression force;
   ii. applying a compression force to the legs and bringing the legs into a substantially parallel position; and iii. nailing the staple into the bone with at least one leg nailed at each side of the epiphyseal plate, whereby the legs exert a expansion force into the bone for lengthening the epiphyseal plate while the cross bar keeps a normal length thereof forming a tether for a periphery of the epiphyseal plate, thus causing the epiphyseal plate to grow around a focus.

2. The method of claim 1, wherein the step of nailing comprises: drilling orifices in the bone for receiving the legs of the staple.

3. The method of claim 1, wherein the step of nailing comprises: nailing the staple directly into the bone by hammering the staple on the bone.

4. The method of claim 1, wherein the staple is made of nitinol and the step of bringing the legs into a substantially parallel position further comprises cooling the staple at a temperature low enough to move the legs to a desired position.

* * * * *